US008216280B2

(12) United States Patent
White

(10) Patent No.: US 8,216,280 B2
(45) Date of Patent: Jul. 10, 2012

(54) MOBILE SPINE STABILIZATION DEVICE

(75) Inventor: Patrick M. White, West Chester, PA (US)

(73) Assignee: K2M, Inc., Leesburg, VA (US)

( * ) Notice: Subject to any disclaimer, the term of this patent is extended or adjusted under 35 U.S.C. 154(b) by 987 days.

(21) Appl. No.: 11/919,778

(22) PCT Filed: May 4, 2006

(86) PCT No.: PCT/US2006/017188
§ 371 (c)(1),
(2), (4) Date: Oct. 31, 2007

(87) PCT Pub. No.: WO2006/119447
PCT Pub. Date: Nov. 9, 2006

(65) Prior Publication Data
US 2009/0131981 A1    May 21, 2009

Related U.S. Application Data

(63) Continuation-in-part of application No. 11/321,337, filed on Dec. 29, 2005, now abandoned, which is a continuation-in-part of application No. 11/244,184, filed on Oct. 5, 2005, now abandoned.

(60) Provisional application No. 60/677,699, filed on May 4, 2005.

(51) Int. Cl.
*A61B 17/70* (2006.01)
*A61B 17/68* (2006.01)

(52) U.S. Cl. ........ 606/264; 606/246; 606/254; 606/262; 606/279

(58) Field of Classification Search .............. 606/60, 606/246, 250–253, 254–257, 258–265, 267–274, 606/279
See application file for complete search history.

(56) References Cited

U.S. PATENT DOCUMENTS

| 5,092,866 | A |   | 3/1992  | Breard et al. |
|-----------|---|---|---------|----------------------------|
| 5,129,753 | A | * | 7/1992  | Wesley et al. ...... 403/322.3 |
| 5,290,289 | A | * | 3/1994  | Sanders et al. ...... 606/279 |
| 5,375,823 | A |   | 12/1994 | Navas |
| 5,480,401 | A |   | 1/1996  | Navas |
| 5,540,688 | A |   | 7/1996  | Navas |
| 5,545,210 | A | * | 8/1996  | Hess et al. ...... 128/898 |
| 5,562,660 | A |   | 10/1996 | Grob |
| RE36,221  | E |   | 6/1999  | Breard et al. |
| 5,938,663 | A |   | 8/1999  | Petreto |
| 5,961,516 | A |   | 10/1999 | Graf |
| 6,016,096 | A | * | 1/2000  | Barnes et al. ...... 337/123 |
| 6,099,528 | A |   | 8/2000  | Saurat |

(Continued)

*Primary Examiner* — Thomas C. Barrett
*Assistant Examiner* — Zade Coley
(74) *Attorney, Agent, or Firm* — Carter, DeLuca, Farrell & Schmidt, LLP

(57) ABSTRACT

An orthopedic device is described for stabilizing the spinal column between first and second vertebral bodies. The device has first and second screws adapted for fixation to the first and second vertebral bodies, respectively. The device further includes an elongated ligament with a first end connected to the first screw and the second end operatively connected with the second screw. The ligament is made preferably of a nickel titanium alloy selected to have ductile inelastic properties at body temperature and is capable of plastic deformation to allow relative constrained motion between the vertebral bodies. The preferred nickel titanium has a martensite/austenite transition temperature above body temperature. In a preferred embodiment, the second pedicle screw includes a bearing for receiving the ligament in a slidably engageable relationship. The device further includes optional first and second dampening members surrounding the ligament for restraining the spinal column during flexion and extension.

9 Claims, 7 Drawing Sheets

U.S. PATENT DOCUMENTS

| | | |
|---|---|---|
| 6,241,730 B1 | 6/2001 | Alby |
| 6,248,106 B1 | 6/2001 | Ferree |
| 6,267,764 B1 | 7/2001 | Elberg |
| 6,293,949 B1 | 9/2001 | Justis et al. |
| 6,423,065 B2 | 7/2002 | Ferree |
| 6,761,719 B2 | 7/2004 | Justis et al. |
| 6,783,527 B2 | 8/2004 | Drewry et al. |
| 6,989,011 B2 | 1/2006 | Paul et al. |
| 7,553,320 B2 * | 6/2009 | Molz et al. .................. 606/247 |
| 7,727,259 B2 * | 6/2010 | Park ............................ 606/255 |
| 2003/0220643 A1 | 11/2003 | Ferree |
| 2004/0215191 A1 | 10/2004 | Kitchen |
| 2004/0236328 A1 | 11/2004 | Paul et al. |
| 2005/0065515 A1 | 3/2005 | Jahng |
| 2005/0065516 A1 | 3/2005 | Jahng |
| 2005/0085815 A1 | 4/2005 | Harms et al. |
| 2005/0124991 A1 | 6/2005 | Jahng |
| 2005/0154390 A1 * | 7/2005 | Biedermann et al. ........... 606/61 |
| 2005/0177156 A1 | 8/2005 | Timm et al. |
| 2005/0203519 A1 * | 9/2005 | Harms et al. .................... 606/61 |
| 2005/0277922 A1 | 12/2005 | Trieu et al. |
| 2006/0036240 A1 | 2/2006 | Colleran et al. |
| 2006/0106381 A1 | 5/2006 | Ferree et al. |
| 2006/0184171 A1 | 8/2006 | Biedermann et al. |
| 2006/0195090 A1 | 8/2006 | Suddaby |
| 2006/0195093 A1 | 8/2006 | Jahng |
| 2006/0212033 A1 | 9/2006 | Rothman et al. |
| 2006/0229612 A1 | 10/2006 | Rothman et al. |

* cited by examiner

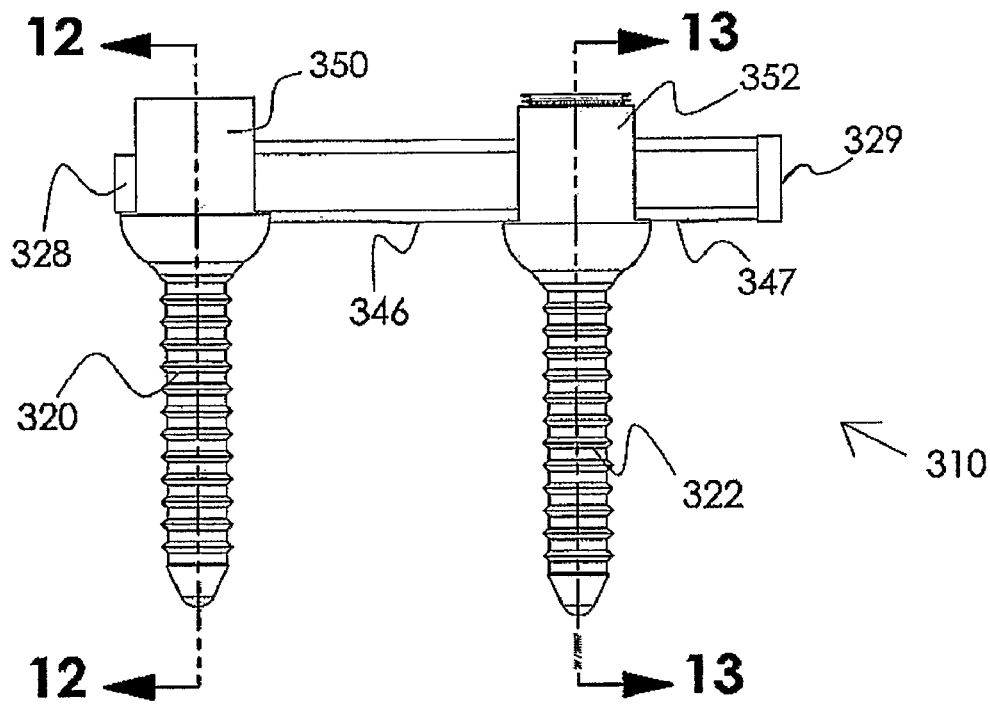
FIG. 11
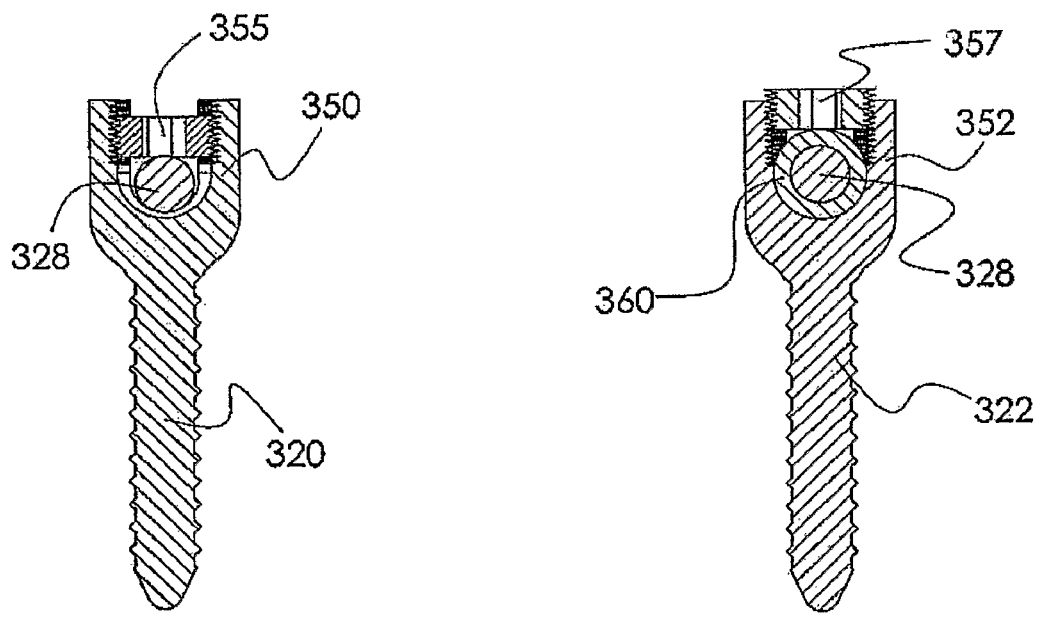
FIG. 12  FIG. 13

MOBILE SPINE STABILIZATION DEVICE

CROSS-REFERENCE TO RELATED APPLICATIONS

This application is a continuation-in-part of U.S. patent application Ser. No. 11/321,337, filed on Dec. 29, 2005, now abandoned which is a continuation-in-part of U.S. application Ser. No. 11/244,184, filed Oct. 5, 2005, now abandoned which claims priority to, and the benefit of, U.S. Provisional Patent Application Ser. No. 60/677,699, filed on May 4, 2005, the entire disclosures of which are expressly incorporated by reference herein.

BACKGROUND OF THE INVENTION

1. Technical Field of the Invention

The present invention relates to orthopedic stabilization devices used to limit the relative motion of at least two vertebral bodies for the relief of pain. These devices can be used to aid osteo-synthesis in combination with fusion devices, supplement other motion restoring devices such as disk implants or used solely to restrict the motion of vertebral bodies without other devices.

2. Description of the Related Art

In the field of spine surgery, there have been many attempts to relieve pain associated with spinal injury or illness. Traditionally surgeons have fused the vertebral bodies with a pedicle screw and rod construct or a fusion cage. In attempting to fuse the patient there is a long and painful recovery process. Most rod and screw constructs and fusion cage constructs are very rigid, not allowing transfer of stress into the fusion site that would otherwise aid in a quicker recovery. These approaches defy Wolfe's law stating: bone that is not stressed will degrade. As a corollary, where stress is allowed to transfer through the fusion site while the vertebral bodies are held in a limited range of motion, then fusion can occur much quicker aiding in patient recovery time.

Many are working to develop devices that allow relative motion, yet these have fallen short in minimizing shear forces between the vertebral bodies being stabilized. Another shortcoming is that relative motion has been forcibly channeled through a rather specific location or hinge point in the mechanical construct. The following discussion more particularly summarizes these efforts.

U.S. Pat. No. 5,092,866, which was reissued as U.S. Re. 36,221, discloses a pedicle screw system that is banded together with flexible ligaments. While the ligaments allow for relative motion, they do not appear to resist compression or shear loads, instead relying upon tension alone.

European Patent No. EP 06691091 A1/B1 and the DYNE-SYS®, a registered trademark of Zimmer GmbH, product brochure disclose a polycarbonate/urethane supporting element, compressed between two adjacent pedicle screws and passing over an elastic strap that acts as a flexible internal ligament. The flexible internal ligament is in the form of a nylon cord, which is pre-tensioned and fastened to the screw heads. This design provides flexural degrees of freedom, allows relative motion between the vertebral bodies, but does little to inhibit or prevent shearing between the vertebral bodies. While flexibility is desirable, the DYNESYS® ligament would appear to lack rigidity and rely on proper tensioning inter-operatively to gain its balance.

U.S. Pat. No. 6,267,764 discloses a pedicle screw and rod system wherein the rod is flexible in translation. A dampening ball is not separate from the rods and has cutouts to allow bending, with no ligament passing through the centers of the rods. While flexibility in translation can be helpful, the spine loads in several planes at the same time and the translation spoken of in this patent would appear to inadequately redistribute stresses through the fusion site. As a result motion is forcibly limited to one location, i.e., motion is constrained through a hinge point, which undesirably stresses the assembly construct.

U.S. Pat. No. 6,241,730 discloses a construction that lacks a ligament element, particularly a ligament extending through the center of rod members. There is a compressible dampening element. The disclosed design attempts to accomplish a multidirectional redistribution of force for aiding in quicker fusion rates, however its constructs were not designed for use in conjunction with a disk implant. The disclosed approach overly limits motion of the vertebral bodies to one location, i.e., forces motion unnaturally through a hinge point.

U.S. Pat. Nos. 6,293,949 and 6,761,719 disclose embodiments seeking to elastically constrain range of motion using a continuous super-elastic nitinol rod and pedicle screw system. Due to the super-elastic state of the rod, motion is always pushed-back to a neutral, pre-set position. This constrains force through the rod in a manner causing early fatigue failure. In order to provide the correct elasticity of the rod, its diameter must be so small that it cannot withstand the continuous loads. Further, the rod cannot be bent at the time of surgery to a preformed shape holding the vertebral bodies in a desired relative position while also limiting their relative motion.

Accordingly, there exists a need for assemblies and devices that effectively resist torsion as well as shear forces while providing flexible spine stabilization. More specifically, it would be desirable to provide kits with such assemblies and devices, which work with existing pedicle screw arrangements.

There is another need for flexible assemblies and devices having rigid members deformable to fit a patient's anatomical contours while maintaining flexibility of the orthopedic construct.

There is yet another need for assemblies and devices to stabilize vertebrae while providing multi-directional flexibility, without imparting elastic stresses to the bone.

There is a further need yet to provide a spine stabilization device that can allow natural flexion and extension motion while effectively restraining torsional and shear forces.

There is a further need to provide spine stabilization assemblies and devices manufactured from a shape memory material such as an alloy or other flexible polymer, which can withstand repeated loading of the spine without fatiguing yet still maintain its flexibility.

SUMMARY OF THE INVENTION AND ADVANTAGES

According to one embodiment of the present invention, there is provided an orthopedic device for stabilizing the spinal column between anchorage locations on respective first and second vertebral bodies. The device includes an elongated bridge having first and second ends operatively connected at the respective anchorage locations. The bridge contains an implantable ligament selected to be inelastic at body temperature. The ligament is further capable of continuous plastic deformation to allow relative constrained motion while resisting forces exerted upon the vertebral bodies. In a one embodiment, the bridge contains an implantable nickel titanium alloy. In another embodiment, the device further includes a dampening member surrounding at least a portion of the ligament. In yet another embodiment, the ligament is in the form of a wire, tube, or band. Preferably, the ligament is made of a nickel titanium alloy having a martensite/austenite transition temperature substantially higher than normal body temperature, and more preferably at least 10 degrees centigrade above normal body temperature. In still another embodiment, the device includes rigid rod members each correspondingly retained with either end of the ligament, and independently attached to the vertebral bodies with anchors. The rigid rod members are correspondingly connected to either end of the ligament. In still yet another embodiment, the device includes a plate segment retained with an end of the ligament and independently attached to a vertebral body with the plurality of anchors; more preferably, a plurality of plate segments are correspondingly connected to either end of the ligament.

In another embodiment of the present invention, an orthopedic device for stabilizing the spinal column includes an elongated implantable ligament with two ends, the ligament partially formed of an implantable nickel titanium alloy capable of continuous plastic inelastic deformation at body temperature. Either end of the ligament is attached to a vertebral body with a screw at an anchor location. A compression-dampening member surrounds the ligament and is sandwiched between the screws. Plastic deformation in the ligament allows relative constrained motion between the vertebral bodies.

In yet another embodiment of the present invention, an orthopedic device for stabilizing the spinal column is disclosed. The device includes an implantable elongated ligament with two enlarged end portions. The ligament is partially formed of a nickel titanium alloy capable of continuous plastic inelastic deformation at body temperature. Two rigid rod members each contain a bore sized for the ligament, the rigid rod members being retained with either end of the ligament and engageable with two vertebral bodies by a plurality of anchors. A compression-dampening member surrounds the ligament and is sandwiched between the rods. Two tension-dampening members are captured within the rigid rod bores, surround the ligament and abut the enlarged end portions respectively. Plastic deformation in the ligament allows relative constrained motion between the vertebral bodies.

In still another embodiment of the present invention, a surgical kit is disclosed. The kit includes at least one bone anchor and a flexible spine stabilization device. The device includes a ligament partially formed of an implantable nickel titanium alloy capable of continuous plastic inelastic deformation at body temperature. In a preferred embodiment, the surgical kit includes at least one rigid fusion rod. The anchor, ligament, and rigid fusion rod mentioned above are provided in various sizes to accommodate a given patient's anatomy.

In a further embodiment, an orthopedic spine stabilization device is disclosed having an elongated ligament with two ends. The ligament is manufactured to exhibit inelastic characteristics at body temperature while further being capable of continuous plastic deformation and can be in the form of a wire, a rod, a tube, a cable, a band, a plate, or a more complex shape such as an I-beam configuration. The device includes a first screw adapted for securely fastening one end of the ligament to a vertebral body and a second screw with a bearing for receiving the opposite end of the ligament securing it in a mobile fashion to another vertebral body. Plastic deformation in the ligament allows relative constrained motion between the vertebral bodies.

In still yet a further embodiment, a spine stabilization device is disclosed with an elongated shape memory nickel titanium ligament having a transformation temperature above body temperature. The nickel titanium ligament in the form of a rod exhibits a ductile characteristic during use allowing motion. In one form of use, the nitinol rod having an martensite/austenite transition temperature above body temperature, and preferably substantially above body temperature, i.e., by at least about 10 degrees centigrade above normal nominal body temperature, i.e., about 98 degrees Fahrenheit or about 37 degrees centigrade, is secured to at least two vertebral bodies such as by spine screws. The screws may be known pedicle screws, such as titanium pedicle screws. Alternatively, one end of the rod may be fixed to one vertebral body with a first screw, and the other end of the rod may be secured to a second vertebral body with a second screw containing a plastic linear bearing. As the body moves the ductile nature of the ligament resists bending and shear motions in the vertebral column while at the same time the rod slides in a translational relationship to the second screw further allowing flexion and extension motions.

In another embodiment of the present invention, an orthopedic device for stabilizing the spinal column is shown. The device includes an elongated shape memory nickel titanium (i.e. nitinol) ligament having a martensite/austenite transformation temperature above body temperature and exhibiting ductile characteristics during use. The ligament is formed in the shape of a rod with first and second ends and the second end includes an abutment. The device also includes a first screw adapted to securely fasten the first end of the rod to a vertebral body and a second screw presenting a plastic linear bearing for receiving the second end of the rod and securing it in a slidably constrained fashion to the other vertebral body. Surrounding the rod and sandwiched between the first and second screw is one dampening member and a second dampening member is found surrounding the rod and sandwiched between the second screw and the abutment. As the body moves, the ductile nature of the ligament resists bending and shear motion in the vertebral column while at the same time the rod can slidably translate in relationship to the second screw allowing flexion and extension motion. The dampening members act as cushions for flexion and extension motions and controllably resist the sliding motion between the ligament and the bearing.

An advantage of the present invention is a device that limits the range of relative motion between two vertebral bodies and works with existing pedicle screw assemblies.

Another advantage of the invention is to constrain the motion between vertebral bodies in a ductile manor.

Another advantage is to allow controlled flexion and extension motions of the spine while constraining bending and shear forces.

Another advantage of the invention is to provide a kit to the surgeon that has a variety of pedicle screws, rigid fusion rods, and elongated implantable ductile ligaments. Further, it is desirable that the ligaments provide a variety of stiffness and flexibility options so the surgeon can select the appropriate stiffness and range of motion to achieve the desired surgical result whether it is for aiding fusion or restoring normal range of motion to a patient.

Other objects and advantages will become apparent to a reader skilled in the art, with reference to the following Figures and accompanying Detailed Description wherein textual reference characters correspond to those denoted on the Drawings.

BRIEF DESCRIPTION OF THE DRAWINGS

In the accompanying drawings:

FIG. 11 is an elevation view of the present invention employing a ligament which is slidably constrained using a pedicle screw and bearing;

FIG. 12 is a sectional view taken longitudinally along Lines 12-12 of FIG. 11;

FIG. 13 is a sectional view taken longitudinally along Lines 13-13 of FIG. 11 showing a pedicle screw with a bearing sleeve;

DETAILED DESCRIPTION OF THE INVENTION

With reference generally to FIGS. 1-15, the Applicant's invention provides flexible spinal stabilization allowing controlled relative vertebral motion for the relief of pain, while minimizing intervertebral shear forces. Moreover, the invention evenly distributes mechanical stresses throughout its structure rather than constraining motion within a limited portion of its structure, by virtue of its distinctive design.

Figure 3:
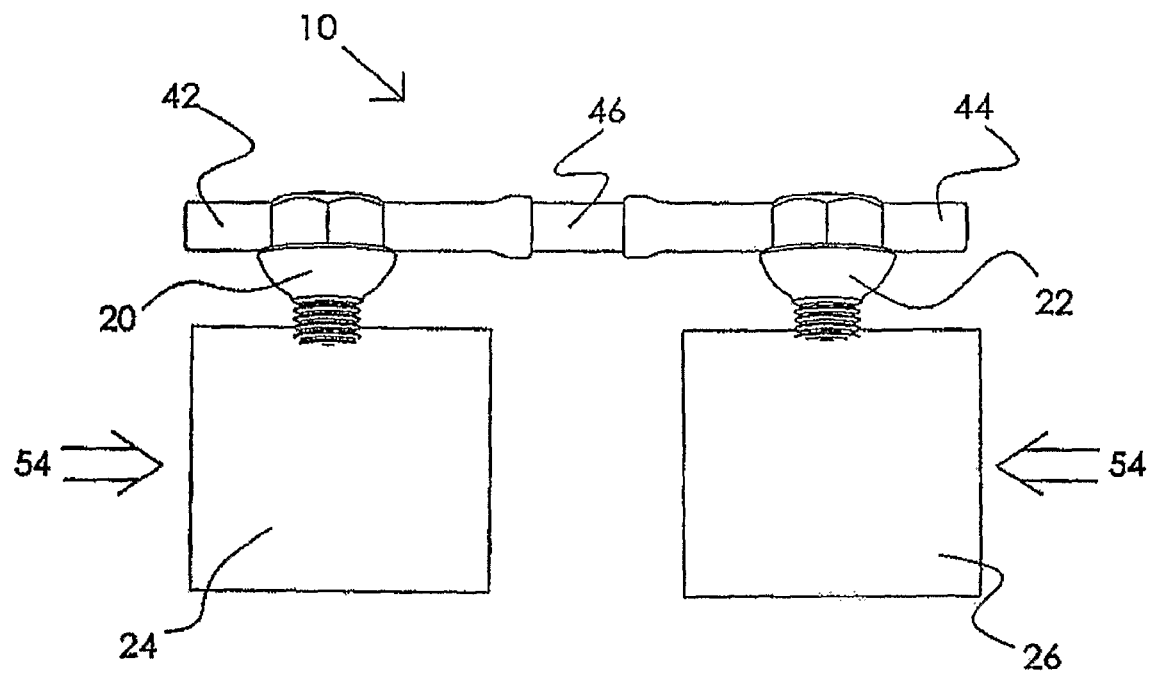
FIG. 3 is an elevational view of the device of FIGS. 1 and 2, further including pedicle screws for attaching the device to adjacent vertebral bodies as schematically shown.
Figure 4:
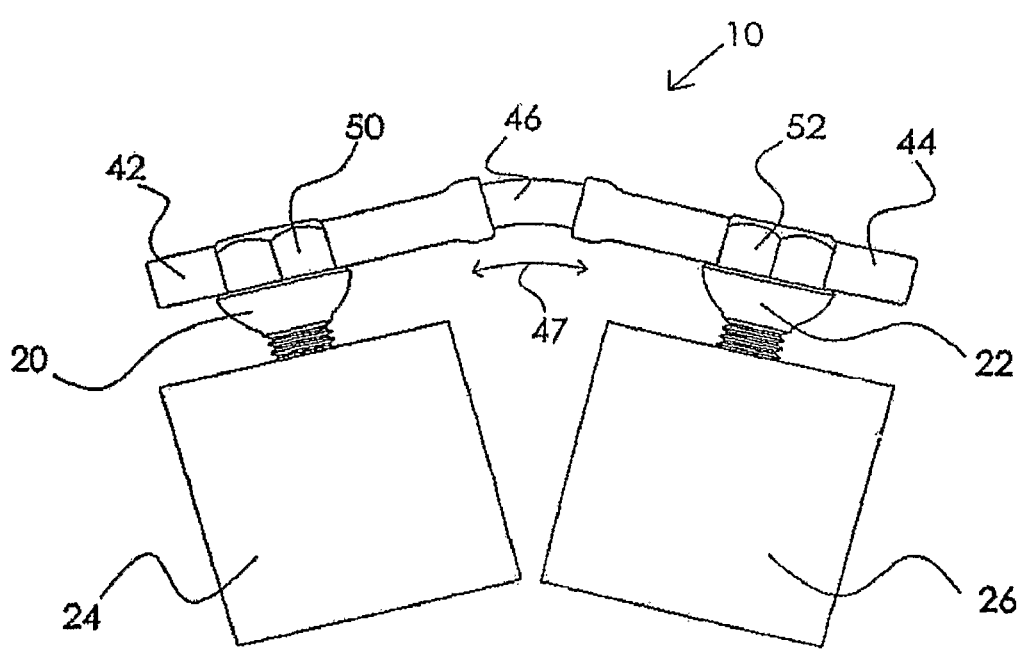
FIG. 4 is an elevational view of the device of FIG. 3, upon application of load.

Referring to FIGS. 1 and 2-4, an elongated bridge member is generally shown as an assembly at 10. Elongated bridge member or assembly 10 includes a ligament 28 shown in the form of a wire. It will be understood that the ligament 28 may also take the form of a tube, a solid rod or a band, having different cross sectional shapes (e.g., round, rectangular, square, I-beam) and sizes (e.g., from about 25 mm in length to over 100 mm in length and varied diameters, thickness or height and width). The ligament 28 is made of an implantable material selected to be inelastic at body temperature and allows relative constrained motion while resisting bodily shear forces. The ligament 28 has opposed first 30 and second 32 ends received within washer type connectors 34, 36 that engage counter-bores 38, 40 formed within rigid rod members 42, 44, respectively. The washer type connectors or washers 34, 36 include respective openings 39, 41. Those in the art will appreciate that the rigid rod members 42, 44 could have differing sizes and/or lengths. Washer-shaped connectors 34, 36 are preferably made of a shape-memory alloy in its super-elastic state at body temperature. Alternatively, other means for attaching the inelastic ligament 28 to rigid rod members 42, 44 may include welding, threading, gluing, or crimping instead of using connectors 34, 36. Thus, assembly 10 operatively functions as a bridge between a first anchor 20 and a second anchor 22, respectively. Ligament 28 is preferably made of an implantable shape memory alloy, more preferably a nickel titanium alloy, which is selected to be inelastic at body temperature. That is, ligament 28 is not in a super-elastic state, but rather has a martensite/austenite transition temperature substantially greater than body temperature. Preferably, assembly 10 may include a dampening member 46 that has an inner diameter 48 surrounding ligament 28. Referring to FIGS. 3-4, first and second screw anchors 20, 22 are adapted for respectively affixing assembly 10 to first and second vertebral bodies 24, 26. Screw anchors 20, 22 include respective screw heads 50, 52.

Figure 1A:
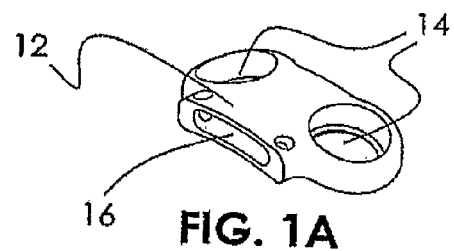
FIG. 1A is a perspective view of a representative plate segment for securing the device of FIG. 1.

Referring to FIG. 1A, a representative plate segment 12 has openings 14 that receive anchoring screws for attachment to a vertebral body not shown. Each plate segment 12 has a passageway 16 configured to receive one end of a ligament not shown. It will be understood that the ligament used in conjunction with the plate 12 could have a variety of forms as elucidated in the above discussion of FIGS. 1 and 2-4. Passageway 16 could have a rectangular cross section as shown, or could have a variety of forms for receiving the ligament. Preferably, a plurality of plates 12 can be employed with the ligament, across a corresponding plurality of vertebral bodies to form a bridge similar to assembly 10 in FIGS. 1 and 2-4.

Referring to FIGS. 3-4, plastic deformation in ligament 28 is in response to external stimulus indicated by arrows 54, 54, which for the sake of illustration is shown as direct uniform axial compression. However, as will be appreciated, the external stimulus often consists of combined bending and twisting motions of a patient's body. Movement of vertebral bodies 24, 26 away from each other, as indicated by arrow 47, causes flexion of dampening member 46.

With continuing reference to FIGS. 1-4, the present assembly 10 resists shear forces exerted between vertebral bodies 24, 26 during the bending and twisting motions of a patient without creating elastic forces that otherwise would exert unnatural stresses forcing the vertebral bodies back into some prior position. The present invention instead allows the body's own motion to return it to the natural position without undue elastic impetus. This natural return to body position is therefore distinct from prior approaches that rely upon super-elastic members such as those discussed above to urge the body to return to a prior position; moreover, the present invention is distinct from prior approaches that do not resist both shear and direct torsional movements while yet bending themselves. The present assembly 10 does not exert resultant forces that are opposite to the motion input 54, 54 and yet the assembly is repetitively plastically deformable due to the material and design employed herein.

Figure 5:
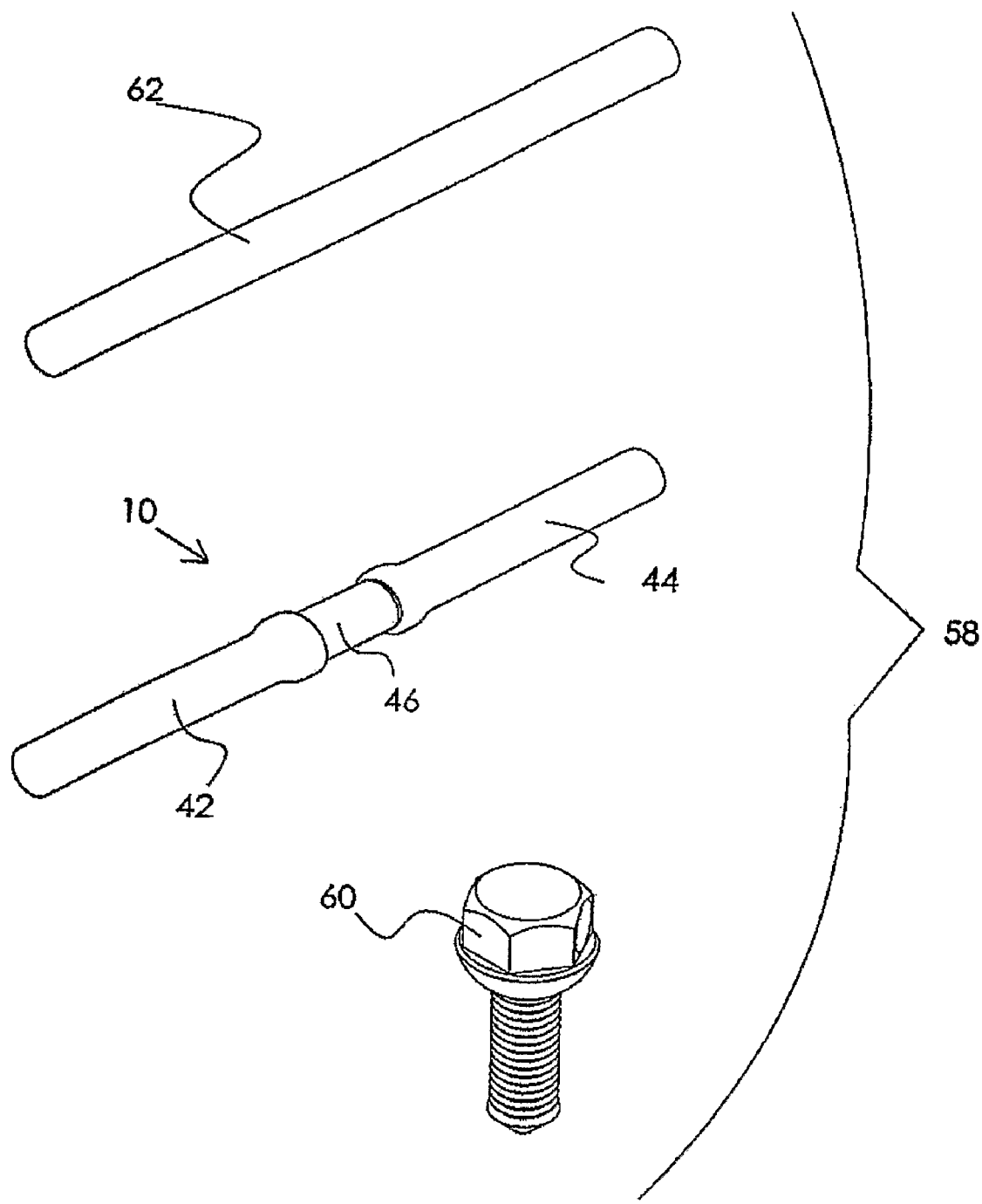
FIG. 5 is a kit of spinal implant components including a pedicle screw, a rigid fusion rod, and a ligament of the present invention, selected from among various ranges of flexibility.

FIG. 5 depicts still another embodiment of the present invention, that is, a surgical kit generally shown at 58. Kit 58 includes an array of bone anchors 60 and an elongated bridge member 10 preferably of the type shown in FIGS. 1-4 although it will be appreciated that an array of assemblies having various sizes and stiffness can be provided. The assembly 10 is capable of continuous plastic inelastic deformation at body temperature. In a preferred embodiment, the surgical kit 58 includes an array of semi-rigid fusion rods such as the representative rod shown at 62. In another preferred embodiment, an alternative surgical kit not shown may include an array of plates similar to those described in conjunction with FIG. 1A. The arrays mentioned above are provided in various sizes to accommodate a given patient's anatomy.

Figure 1:
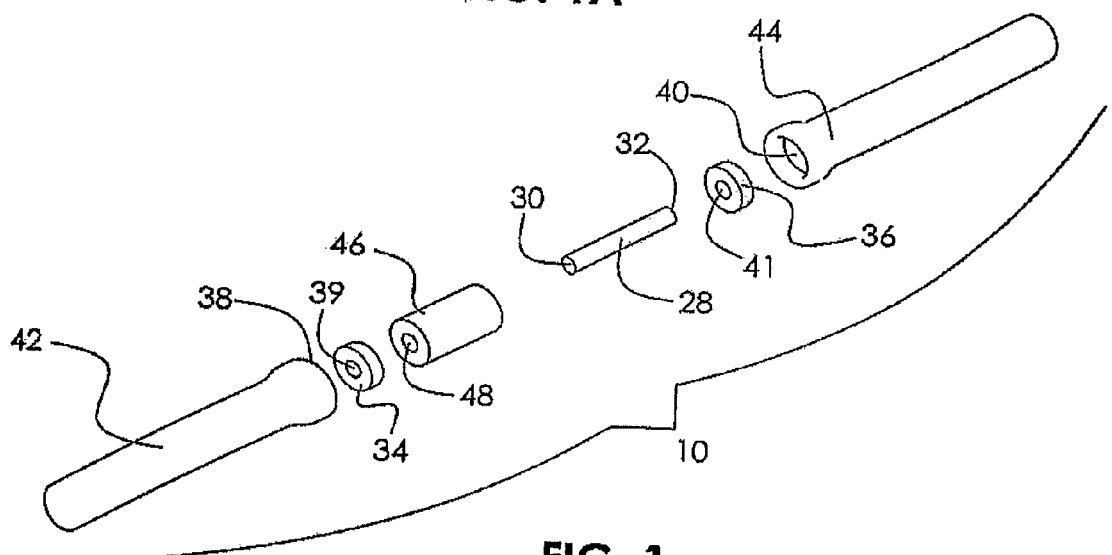
FIG. 1 is an exploded perspective view of an elongated bridge member, according to the present invention.
Figure 2:
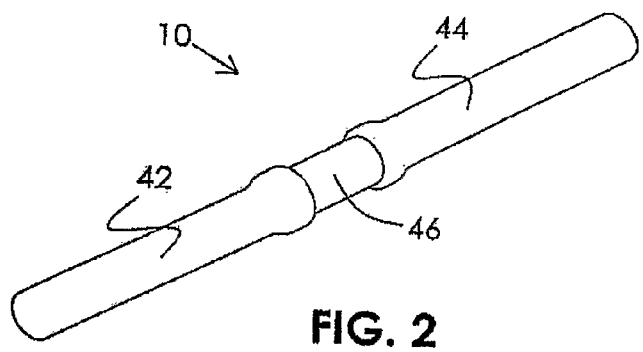
FIG. 2 is a perspective view of the device of FIG. 1, shown in its assembled state.
Figure 6:
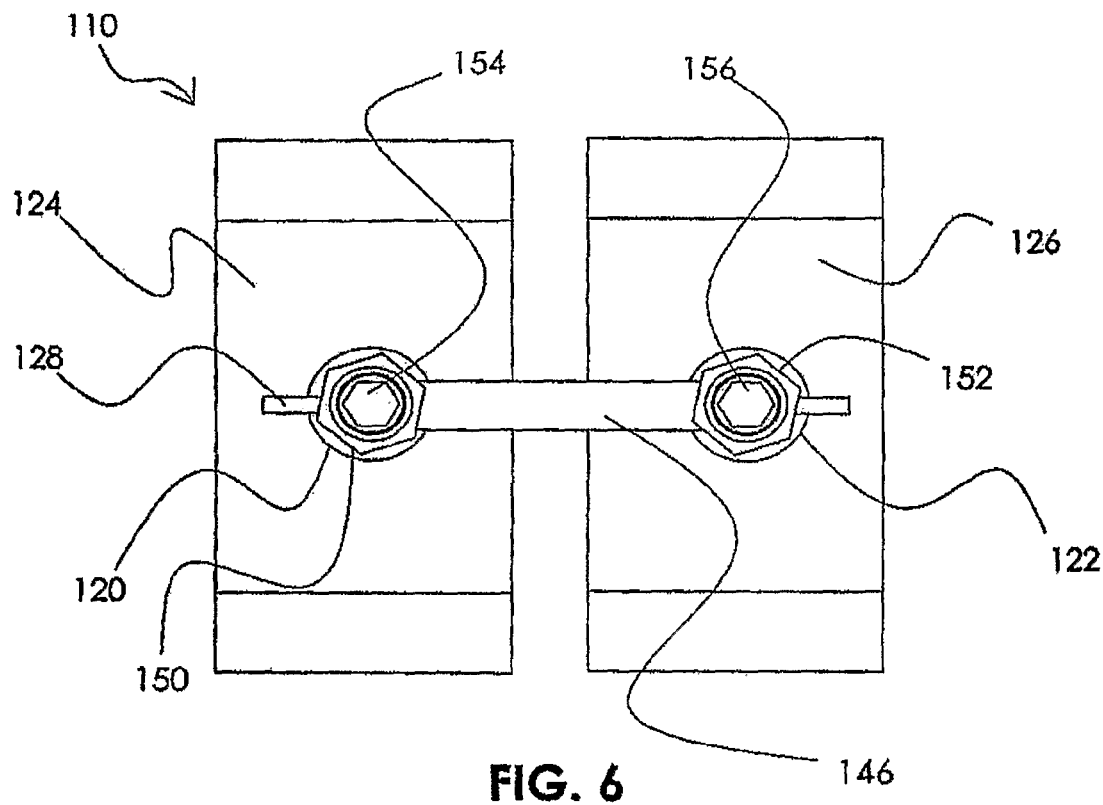
FIG. 6 is a top view of a device employing an elongated implantable ligament attached to vertebral bodies (schematically shown) with pedicle screws that directly secure the ligament between the screws.
Figure 7:
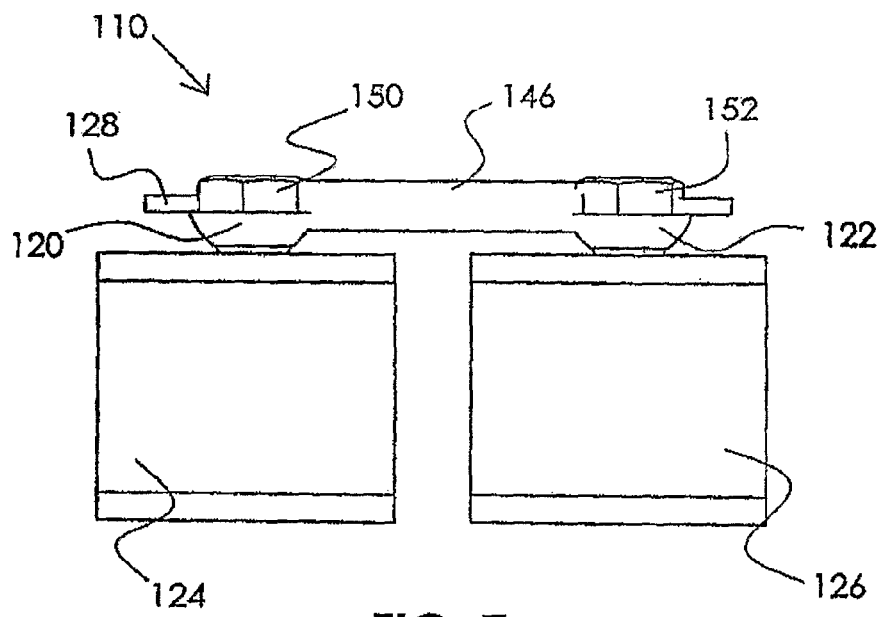
FIG. 7 is an elevational view of the device of FIG. 6.

Referring to FIGS. 6-7, an orthopedic device 110 for stabilizing the spinal column includes an elongated bridge member that takes the form of ligament 128 instead of the assembly 10 as previously discussed in conjunction with FIGS. 1 and 2-4. It will be understood that the ligament 128 may also take the form of a tube, a solid rod, or a band, having different cross sectional shapes, lengths, and sizes. The ligament 128 is at least partially made of an implantable material that is preferably a nickel titanium alloy capable of continuous plastic inelastic deformation at body temperature in similar fashion as ligament 28 (FIG. 1). Device 110 has no distinct rigid rod members as depicted, for example, at 42 and 44 in FIGS. 1 and 2-4. Nor are there any plate segments as at 12 in FIG. 1A to operatively anchor ligament 28. Instead, ligament 128 extends between and directly interconnects screws 120, 122, which affix it to vertebral bodies 124 and 126. An optional compression-dampening member 146 is shown surrounding ligament 128 and is sandwiched between the screw heads 150, 152 in FIGS. 6-7. Plastic deformation of the ligament 128 allows relative motion while minimizing shear stresses between vertebral bodies 124, 126. FIGS. 6-7 show a tubular dampening member 146 preferably made of an in implantable elastomer such as silicone or polycarbonate urethane, through which elongated ligament 128 passes. Screw heads 150, 152 include threaded openings at one end for receiving, respectively, set screws 154, 156. Additionally, each screw head 150, 152 is configured to receive at least a portion of ligament 128 therethrough. Set screws 154, 156 are adapted for securing ligament 128 to its respective screw head 150, 152.

Figure 8:
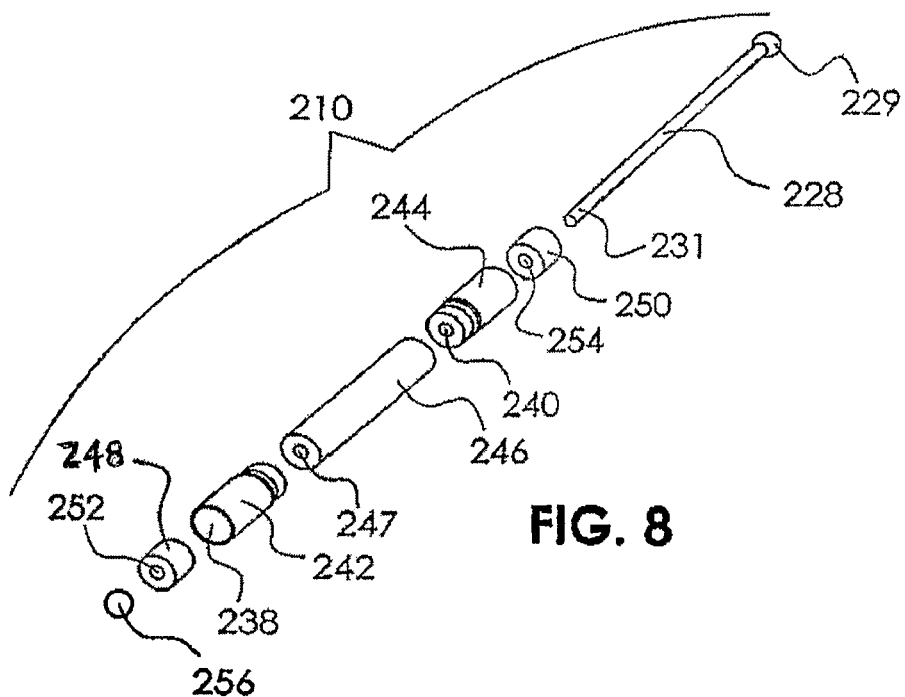
FIG. 8 is an exploded perspective view of another device of the present invention, employing a ligament surrounded by compression and tension-damping members.
Figure 9:
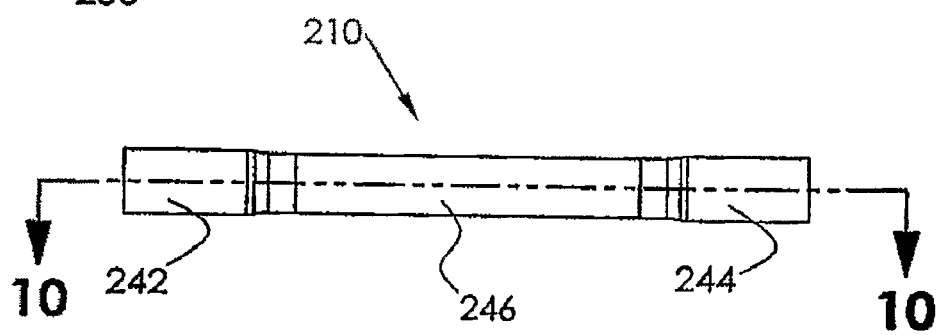
FIG. 9 is an elevational view of the assembled structures shown in FIG. 8 prior to application of a load.
Figure 10:
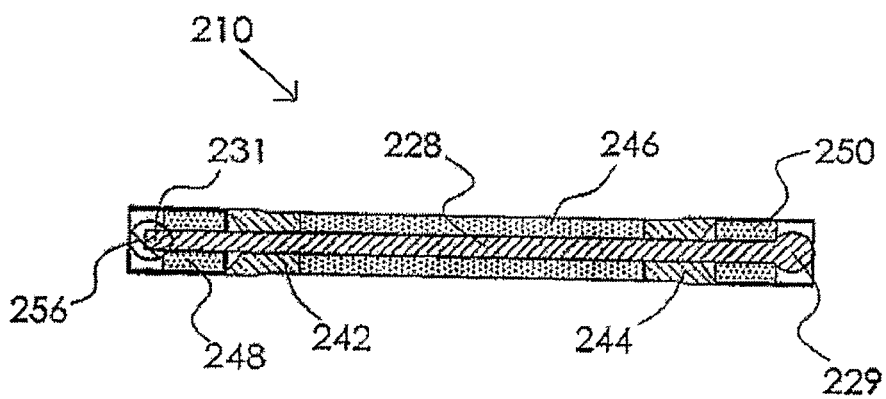
FIG. 10 is a sectional view taken longitudinally along Lines 10-10 of FIG. 9.

Referring to FIGS. 8-10 there is yet another embodiment of the present invention. An elongated bridge member is shown in the form of an assembly 210, for stabilizing the spinal column. Assembly 210 includes an elongated ligament 228 with an enlarged fixed end portion 229 and a free end 231. Ligament 228 is at least partially formed of an implantable inelastic material, preferably nickel titanium alloy capable of continuous plastic inelastic deformation at body temperature, i.e., not in a super-elastic state. Bore 240 of rigid rod member 244 is sized for passage of ligament 228, the rod members 242, 244 are retained with ends 229, 231 of the ligament 228 for attachment at respective anchorage locations to vertebral bodies (not shown). Those in the art will appreciate that the rigid rod members 242, 244 could have differing sizes and/or lengths. A compression-dampening member 246 has a bore 247 that surrounds ligament 228 and is sandwiched between proximally chamfered rigid rod members 242, 244. Tension-dampening members 248, 250 have respective bores 252, 254 sized to allow passage of ligament 228 housed within the bores of the rigid rods 242, 244. Tension-dampening members 248, 250 surround ligament 228 and are respectively captured by rigid rods 242, 244 along with enlarged ends 229, 256 as shown in FIG. 10. Plastic deformation in ligament 228 allows relative constrained motion between, while resisting shear forces exerted upon the vertebral bodies. Motion is transmitted along the entire length of ligament 228 from its enlarged fixed ends 229, 256. Dampening members 246, 248, 250 are preferably made of an implantable elastomer such as silicone or polycarbonate urethane.

Inelastic ligament 28, 128, 228 is preferably manufactured from a nickel titanium alloy preferably having a diameter in the range of 3-6 mm. Other cross sectional shapes and sizes of ligament 28, 128, 228 may be made available for different surgical applications. Nickel titanium can be alloyed to have varying properties, some alloys exhibiting super-elastic behavior at body temperature while other alloys are continuously inelastic at body temperature. These inelastic alloys are commonly referred to as shape memory alloys by those skilled in the art. Shape memory alloys may further have martensite/austenite transition temperatures either above or below body temperature; however, the applicable transition temperature for the present invention is selected to be higher than body temperature, and preferably substantially higher than body temperature. The present inventor has determined that within the operative size range, inelastic ligaments 28, 128, 228 made from shape memory alloys having a martensite/austenite transition temperature above body temperature, exhibit acceptable fatigue resistance. This is because there are no elastic forces exerted by the ligament 28, 128, 228 of the present invention, against the body. It is intended that a surgeon determine how much inelastic resistance is necessary for each individual patient's needs and then pre-selects an assembly or device 10, 110, 210 at the time of surgery to ensure the optimal resistance to deformation. Preferably, the ligament 28, 128, 228 is non-braided and is formed as a unitary contiguous member enabling the ligament to resist shear forces. In the instance where a surgeon may be supplementing fixation of two vertebral bodies 24, 26 and 124, 126 with an interbody implant such as a fusion cage (not shown), a flexible inelastic assembly or device 10, 110, 210 with pedicle screws 20, 22 and 120, 122 is preferable to limit motion and allow stress transfer through the fusion site in accordance to Wolfe's law. In this instance the surgeon would select a less flexible assembly or device 10, 110, 210 with a larger inelastic ligament 28, 128, 228 such as a rod form of ligament in the range of about 5-6 mm in diameter. The diameter and length of the inelastic ligament 28, 128, 228 determine the flexibility of the surgical construct. In another instance, a surgeon may selectively remove the fascia from two adjacent vertebral bodies 24, 26 and 124, 126 to eliminate arthritis caused by bony contact at the fascia. To replace the support for the vertebral bodies after the fasciectomy the surgeon would use a more flexible inelastic assembly or device 10, 110, 210 with pedicle screws 20, 22 and 120, 122 to ensure that axial spacing between posterior segments (not shown) of vertebral bodies 24, 26 and 124, 126 is maintained. In this instance, it would be preferable for the surgeon to select a more flexible assembly or device 10, 110, 210 that has an inelastic ligament 28, 128, 228 such as a rod form of ligament with a diameter closer to about 3-4 mm. This surgical construct would allow a patient to have constrained motion but would limit contact between the fascia of the two vertebral bodies 24, 26 and 124, 126. The rigid rod members 42, 44 and 242, 244 are typically manufactured from stainless steel or titanium and are preferably in the diameter range of 4-7 mm. This size range is typical of other commercially available spinal implant hardware so that flexible inelastic assembly or device 10, 110, 210 of the present type is universally received by existing pedicle screws 20, 22 and 120, 122.

FIGS. 3-7 illustrate use of pedicle screws 20, 22 and 120, 122 to fasten the flexible assembly 10 or device 110 to vertebral bodies 24, 26 or 124, 126. However, other attachment means are possible as well as a variety of alternate locations for mounting. In a traditional spinal stabilization system, the rods are placed posterior to and on either side of the spinous process. Depending on the pathology observed, a surgeon might select a unitary flexible ligament 128 or assembly 10 to mount posterior to the theoretical centerline of a patient between two spinous processes. Alternatively, two or more flexible ligaments may be implanted posteriorly in either side of the posterior spinous processes across the pedicles of adjacent vertebral bodies. Alternatively, one or more flexible inelastic ligaments 128 or assemblies 10 may be placed on the anterior side of the vertebral bodies 24, 26; 124, 126.

Referring to FIGS. 11-13 an embodiment is shown with a device 310 allowing the spine to bend under dynamic constraint. As seen in FIGS. 11-12 a first pedicle screw 320 is designed to be mounted in a first vertebral body (not shown). The pedicle screw 320 has a head portion 350 which is designed to receive the ligament 328 securely with a set screw 355 or any other locking mechanisms that lock the ligament 328 to the screw 320. The ligament 328 is being shown in the form of a rod, however it is important to realize that the form of the ligament is not as important as its mechanical characteristics and could be made in the shape of wire, tube, cable, band, plate, or other suitable shape. Preferably, the ligament 328 should be made from a material that can withstand repeated cyclical loading without failing and should have a ductile nature while at body temperature. Nickel and titanium or nickel titanium as it is referred to can be alloyed to result in a material property that has this ductility, which can also be classified as having an inelastic behavior with continuous plastic deformation. Nickel titanium is known to be manufactured in two general categories. The first is super-elastic; these alloys have an elastic behavior at body temperature but for this application reapply unwanted stresses into the vertebral column during motion and are undesirable. The additional stresses also lead to lower fatigue resistance during use. The second category of nickel titanium alloy (i.e. nitinol) is classified as having a shape memory characteristic. The temperature at which the material will exhibit the memory characteristics is set during the manufacturing process and this temperature is often referred to as the transition temperature at which a phase transformation between martensite and austenite occur, i.e., the martensite/austenite transition or transformation temperature. For this application, it is desirable to set the transition temperature above body temperature, preferably substantially above body temperature. It is known that the higher the transition temperature of the material the higher the fatigue resistance. So, below the transition temperature the ligament 328 can be bent with restraint and takes on a ductile nature allowing it to be reshaped on a continuous basis without fatiguing, allowing it to support the mobile spinal column. In FIGS. 11 and 13 a second pedicle screw 322 is shown for adaptation to another vertebral body (not shown), however both pedicle screws 320, 322 could also be used to treat a fracture within one vertebral body when the bone is fractured or cut into two or more fragments. The second pedicle screw 322 is adapted with a bearing 360 which can be manufactured from any known implantable bearing material such as plastic, metal or ceramic. If a plastic were selected, polyethylene or polyetheretherketone materials have shown good characteristics as a bearing material in orthopedic devices. The bearing 360 can be manufactured as an integral part of the pedicle screw 322 for instance as a simple hole (not shown) drilled through the head 352, or the bearing can be mounted with a set screw 357 as shown. The bearing 360 can be in the form of a ring, washer, ball, or any other bearing that will allow the ligament 328 to be received and allow relative movement between the ligament and the pedicle screw 322 during use. As can be appreciated, the bearing 360 could be fully closed or split to accommodate the relative motion and could be used to receive other rods known in the art. For instance, titanium alloy rods 62 shown in the kit 58 in FIG. 5 used for fusion could be received within the bearing 360 to allow slight relative movement between the pedicle screws 320, 322. It is contemplated that other bridge members such as plastic rods currently under development could also be used in conjunction with the bearings 360 and this description should not be limiting in nature. The ligament 328 can be manufactured to have an abutment 329 and the ligament can receive optional dampening members 346, 347. While the bearing 360 allows relative movement between the pedicle screws 320, 322 in flexion and extension of the spinal column the optional dampening members 346, 347 are useful for additional constraint. The first dampening member 346 can be sandwiched between the head 350 of the first pedicle screw 320 and the head 352 of pedicle screw 322. This first dampening member 346 is used to constrain motion while the spinal column is in extension. The second dampening member 347 surrounds the ligament 328 and is sandwiched between the head 352 of the pedicle screw 322 and the abutment 329. The second dampening member 347 can be used to constrain motion in flexion.

Figure 14:
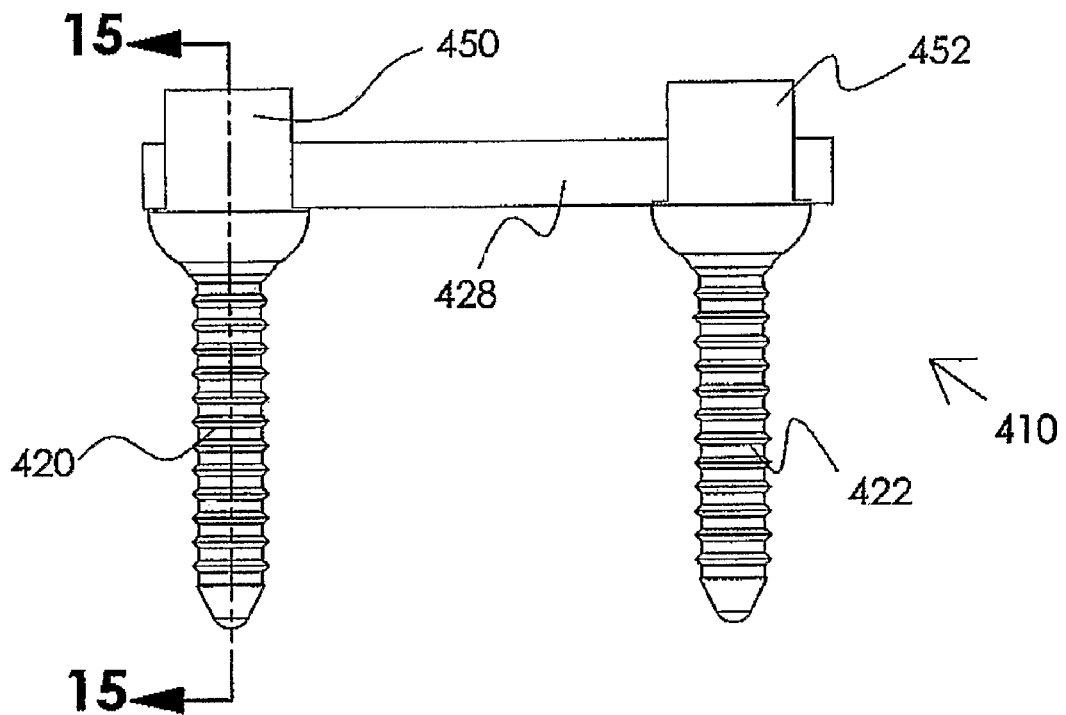
FIG. 14 is a preferred embodiment of the present invention employing a ligament and screws for anchoring.
Figure 15:
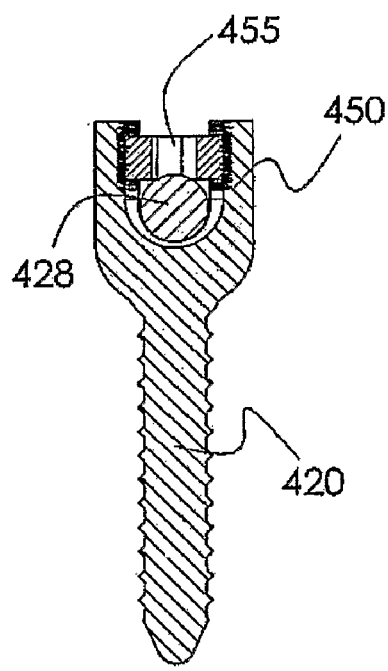
FIG. 15 is a sectional view taken longitudinally along Lines 15-15 of FIG. 14.

Referring to FIGS. 14-15 a preferred embodiment is shown with a device 410 allowing the spine to bend under dynamic constraint. A first screw 420 is designed to be mounted in a first vertebral body (not shown), while a second screw 422 is designed to be mounted in a second vertebral body (not shown). Typically, these screws 420, 422 are mounted in the pedicle region of the bone on the posterior side however, it is contemplated that the mounting could occur on the anterior side of the vertebrae or on, into or between the spinous process allowing a minimally invasive approach for the surgeon. The anchoring means shown would be a preferable way to connect to the vertebrae to the rod 428. Neither the method of attachment nor the shape of the rod should be limiting to the scope of the invention. Screws 420, 442 have respective head portions 450, 452 which are designed to receive a ligament in the form of a rod 428 securely with a set screw 455 or any other locking mechanisms that locks the rod 428 to the screw 420, 422. The rod 428 is being shown with a round cross section used for lower lumbar applications and should be in the range of 3 to 6.5 millimeters in diameter for it to work with existing screw designs. For applications in the cervical spine, the rods should be sized in the range of 1 to 4.5 millimeters in diameter. In FIG. 14 a second screw 422 is shown for adaptation to another vertebral body (not shown), however both screws 420, 422 could also be used to treat a fracture within one vertebral body when the bone is fractured or split into two or more fragments.

Preferably, the rod 428 should be made from a material that can withstand repeated cyclical loading without failing and should have a ductile nature while at body temperature. Nickel and titanium or nickel titanium, nitinol as it is referred to, can be alloyed to result in a material property that has this ductility which can also be classified as having an inelastic behavior with continuous plastic deformation. Nickel titanium is known to be manufactured in two general categories.

The first is super-elastic; these alloys have an elastic behavior at body temperature and undergo a phase transformation from austenite to martensite by way of stress, sometimes referred to as stress induced martensite. Others have tried applying this type of material to rods and plates for spinal applications, however the devices work as a giant spring which applies unwanted stresses into the vertebral column during motion. The additional stresses also lead to lower fatigue resistance during use and ultimate failure due to the fact that the construct repeatedly transitions through the phase changes as it is loaded and unloaded.

The second category of nickel titanium is classified as having a shape memory characteristic. The temperature at which the material will exhibit the memory characteristics is set during the manufacturing process and is referred to as the transition temperature at which a phase transformation between martensite and austenite occur. In most applications, the shape memory nickel titanium is selected to take advantage of a temperature induced phase change; however, that is not the case for the instant invention. Thus, unlike prior uses of nickel titanium alloys for spinal implant constructs, devices in accordance with the present disclosure do not utilize either the super-elastic or the shape memory characteristics of these alloys. Because the phase transition temperature of the selected nickel titanium alloy is chosen to be substantially higher than body temperature, the alloy remains in the martensite state at all times during use. Because the material is in its martensite state at body temperature, loading of the rod or ligament cannot induce a phase change from austenite to martensite as the material is at all times during use in the martensite state. Similarly, because the phase transition temperature is substantially above body temperature, the temperature induced shape memory effect is not utilized. Indeed, any attempt to heat the material above the phase transition temperature would have undesirable detrimental effects on surrounding tissue.

As stated, it is desirable in this case to use shape memory nickel titanium with a transition temperature significantly above the use temperature which is body temperature so the material always remains in its martensitic state ensuring that no phase transformation occurs. The martensitic state allows the material to take on the desired ductile inelastic behavior as described without stress or temperature induced phase transformation. The greater the difference between the transition temperature and the use temperature the higher the fatigue resistance, and the transition temperature preferably is set somewhere between 120 and 320 degrees Fahrenheit (49 to 160 degrees centigrade) which is well above body temperature (i.e., nominally about 98 degrees Fahrenheit or about 37 degrees centigrade). A rod having a phase transition temperature of about 200 degrees Fahrenheit (95 degrees centigrade) has demonstrated desirable properties, as discussed below in connection with Example 1.

Example 1

A single level spinal construct consisting of a pair of nitinol rods each 76 mm in length and 5.5 mm in diameter and having a martensite/austenite transition temperature of 200 degrees Fahrenheit (95 degrees centigrade) was prepared using DENALI™ spinal screws (available from K2M, LLC, Leesburg, Va., under the designation K2M 40) was tested pursuant to ASTM testing standard F 1717-04 (Spinal Implant Constructs in a Verbrectomy Model). The results are shown in Table 1.

TABLE 1

| Test Number | Nominal Load During Test (Newtons) | Cycles | Result |
| --- | --- | --- | --- |
| 1 | +/−110 N (+/−5 N variance) | 5,000,000 | Runout |
| 2 | +/−110 N (+/−5 N variance) | 5,000,000 | Runout |

The results reported in Table 1 show that a 5.5 mm diameter nitinol rod having a martensite/austenite transition temperature of about 200 degrees Fahrenheit (95 degrees centigrade) can withstand 5 million cycles at 110 N load.

The present invention is by no means restricted to the above-described preferred embodiments, but covers all variations that might be implemented by using equivalent functional elements or devices that would be apparent to a person skilled in the art, or modifications that fall within the spirit and scope of the appended claims.

What is claimed is:

1. An orthopedic construct for stabilizing the spinal column between respective first and second vertebral bodies, the construct comprising:
   an elongated rod with opposed first and second ends, the rod at least partially formed of an implantable nickel titanium alloy having a martensite/austenite transition temperature of at least about 95 degrees centigrade, so that the rod is capable of plastic deformation at body temperature;
   a first anchoring screw attachable to a first vertebral body; and
   a second anchoring screw attachable to a second vertebral body, wherein the first end of the rod is coupled to the first anchoring screw and the second end of the rod is coupled to the second anchoring screw; wherein each of the anchoring screws includes a threaded shaft capable of engaging bone and a head having a generally U-shaped recess for receiving the rod.

2. The orthopedic construct of claim 1 wherein the transition temperature is in the range of about 95 to 160 degrees centigrade.

3. The orthopedic construct of claim 1, wherein the rod remains in the martensite state while disposed in the body.

4. The orthopedic construct of claim 1, wherein the rod is coupled to the respective anchoring screw with a setscrew.

5. The orthopedic construct of claim 1, wherein the rod has a diameter of about 3 mm to about 6 mm.

6. A method of stabilizing bones relative to each other comprising:
   securing a first end of an elongated ligament adjacent to a first bone and a second end of the elongated ligament adjacent to a second bone, the ligament being made from a nickel titanium alloy having a martensite/austenite transition temperature of at least about 95 degrees centigrade so that the ligament is capable of plastic inelastic deformation at body temperature.

7. The method of claim 6, wherein the step of securing the first and second ends of the ligament further comprise securing the ends to both with bone screws.

8. The method of claim 6, wherein the ligament remains in the martensite state while disposed in the body.

9. The method of claim 6, wherein said step of securing first and second ends of an elongate ligament relative to bones comprises securing a ligament having a transition temperature in the range of about 95 to 160 degrees centigrade.

* * * * *